United States Patent
Peng (10) Patent No.: US 11,372,225 B2
(45) Date of Patent: Jun. 28, 2022

(54) MIRROR IMAGE MICROSCOPIC IMAGING DEVICE, AND MICRONEEDLE ATTITUDE CALIBRATION SYSTEM AND METHOD

(71) Applicant: HUNAN CHANGSHA OURTOOL BIOLOGICAL TECHNOLOGY CO., LTD., Changsha (CN)

(72) Inventor: Jianjun Peng, Changsha (CN)

(73) Assignee: HUNAN CHANGSHA OURTOOL BIOLOGICAL TECHNOLOGY CO., LTD., Changsha (CN)

( * ) Notice: Subject to any disclaimer, the term of this patent is extended or adjusted under 35 U.S.C. 154(b) by 335 days.

(21) Appl. No.: 16/467,034

(22) PCT Filed: Aug. 22, 2018

(86) PCT No.: PCT/CN2018/101669
§ 371 (c)(1),
(2) Date: Jun. 5, 2019

(87) PCT Pub. No.: WO2019/042198
PCT Pub. Date: Mar. 7, 2019

(65) Prior Publication Data
US 2019/0302438 A1    Oct. 3, 2019

(30) Foreign Application Priority Data

Sep. 2, 2017    (CN) .......................... 201710782364.3

(51) Int. Cl.
*G02B 21/32*    (2006.01)
*G02B 21/00*    (2006.01)
(Continued)

(52) U.S. Cl.
CPC ......... *G02B 21/0088* (2013.01); *C12M 21/06* (2013.01); *G02B 21/00* (2013.01);
(Continued)

(58) Field of Classification Search
CPC .... G02B 21/00; G02B 21/0088; G02B 21/24; G02B 21/26; G02B 21/32; G02B 21/34; C12M 21/06; C12M 23/42; A61D 19/02
(Continued)

(56) References Cited

U.S. PATENT DOCUMENTS 4,606,616 A * 8/1986 Parker .................. G02B 21/125
359/383
4,682,864 A    7/1987 Kakii et al.
(Continued)

FOREIGN PATENT DOCUMENTS

CN    202583591 U    12/2012
CN    103249829 A    8/2013
(Continued)

OTHER PUBLICATIONS

International Search Report dated Nov. 30, 2018 in the corresponding international application (application No. PCT/CN2018/101669).

(Continued)

*Primary Examiner* — Thong Q Nguyen
(74) *Attorney, Agent, or Firm* — Kilpatrick Townsend & Stockton LLP (57) ABSTRACT

There are provided a microscopic mirror imaging device, a system and a method for calibrating a posture of a microneedle. The microscopic mirror imaging device includes a motion actuator, a mirror image former support and a mirror image former. The motion actuator is fixedly mounted on a microscope stage. One end of the mirror image former support is connected to the motion actuator. The mirror image former includes a plane mirror mounted on the other end of the mirror image former support. An angle formed between a mirror surface of the plane mirror and a horizontal plane of the microscope stage is equal to (Continued)

45°, and an angle formed between the mirror surface of the plane mirror and a coronal plane of the microscope stage is equal to 45°.

5 Claims, 12 Drawing Sheets

(51) Int. Cl.
*C12M 3/00* (2006.01)
*G02B 21/26* (2006.01)
*A61D 19/02* (2006.01)

(52) U.S. Cl.
CPC .............. *G02B 21/26* (2013.01); *A61D 19/02* (2013.01); *C12M 23/42* (2013.01)

(58) Field of Classification Search
USPC ........................................ 359/368–398, 871
See application file for complete search history.

(56) References Cited

U.S. PATENT DOCUMENTS

| 7,394,593 | B2 * | 7/2008 | Rottermann | G02B 21/086 |
|---|---|---|---|---|
| | | | | 359/232 |
| 2013/0143200 | A1 | 6/2013 | Sun et al. | |
| 2014/0118820 | A1 | 5/2014 | Kaneki et al. | |
| 2015/0031012 | A1 | 1/2015 | Palermo | |
| 2015/0360236 | A1 | 12/2015 | Garcia et al. | |

FOREIGN PATENT DOCUMENTS

| CN | 104254596 | A | 12/2014 | |
|---|---|---|---|---|
| CN | 204086696 | U | 1/2015 | |
| CN | 204287065 | U | 4/2015 | |
| CN | 107357031 | A | 11/2017 | |
| CN | 207216133 | U | 4/2018 | |
| DE | 4008072 | C1 | 11/1991 | |
| JP | H01217307 | A | 8/1989 | |
| JP | H03230105 | A | 10/1991 | |
| JP | H0964124 | A | 3/1997 | |
| JP | 2007155448 | A | 6/2007 | |
| JP | 5010793 | B2 | 8/2012 | |
| WO | 2009005368 | A1 | 1/2009 | |
| WO | WO-2013068642 | A1 * | 5/2013 | ................ B25J 7/00 |

OTHER PUBLICATIONS

JP First Office Action dated Feb. 25, 2020 in the corresponding JP application(application No. 2019-546967).
Hubert Joris: "Hydraulic Manipulators for ICSI" In: "Practical Manual of In Vitro Fertilization", Jan. 1, 2012 (Jan. 1, 2012), Springer New York, New York, NY, XP055639722, ISBN: 978-1-4419-1780-5 pp. 329-334, DOI: 10.1007/978-1-4419-1780-5_35.
Liu Jun et al.: "Robotic Adherent Cell Injection for Characterizing Cell-Cell Communication", IEEE Transactions on Biomedical Engineering, vol. 62, No. 1, Jan. 1, 2015 (Jan. 1, 2015), pp. 119-125, XP011568290, ISSN: 0018-9294, DOI: 10.1109/ TBME.2014. 2342036 [retrieved on Dec. 18, 2014].
Anonymous: "Motorized Filter Flip Mounts", Apr. 9, 2016 (Apr. 9, 2016), XP055639954, Retrieved from the Internet: URL:https://web.archive.org/web/20160409092541/http://www.thorlabs.com/newgrouppage9.cfm objectgroup_ID=3962 [retrieved on Nov. 7, 2019], 2 pages.
Anonymous: "OPX2400/M Two-position mirror slider", Oct. 28, 2016 (Oct. 28, 2016), XP055639989, Retrieved from the Internet: URL:https://www.thorlabs.com/drawings/f2d222a2cf9b9e5-B2504EAC-B6B3-B41C-9006C3E78779A3D6/0PX2400 MAutoCADPDF.pdf [retrieved on Nov. 7, 2019], 1 page.
European Search Report dated Nov. 21, 2019 in the corresponding EP application (application No. 18850693.5).
Russian Search Report dated Nov. 12, 2019 in the corresponding Russian application (application No. 2019118977/28.
Zsolt Peter Nagy et al., "Practical Manual of In Vitro Fertilization", Advanced Methods and Novel Devices, 684 pages.
Zhe Lu et al., "Robotic ICSI (Intracytoplasmic Sperm Injection)", Article in IEEE transactions on bio-medical engineering, in Jul. 2011, 8 pages.

* cited by examiner

MIRROR IMAGE MICROSCOPIC IMAGING DEVICE, AND MICRONEEDLE ATTITUDE CALIBRATION SYSTEM AND METHOD

CROSS-REFERENCE TO RELATED APPLICATIONS

The present application is the national phase of PCT International Patent Application PCT/CN2018/101669, filed on Aug. 22, 2018 which claims the priority to Chinese Patent Application No. 201710782364.3, titled "MIRROR IMAGE MICROSCOPIC IMAGING DEVICE, AND AUTOMATIC MICRONEEDLE ATTITUDE CALIBRATION SYSTEM AND METHOD", filed on Sep. 2, 2017 with the Chinese Patent Office, both of which are incorporated herein by reference in their entireties.

FIELD

The present disclosure relates to the field of microscopic instruments, and in particular to a microscopic mirror imaging device, and a system and a method for calibrating a posture of a microneedle.

BACKGROUND

An inverted microscope is an important instrument used in biological laboratories and functions as an indispensable tool in the field of microscopy. Among methods for male factor infertility, the intracytoplasmic sperm injection (ICSI) technology as an insemination method is widely used in the world. In a conventional ICSI method, the ICSI process is performed by manually operating a micromanipulation device. A method for selecting a sperm and performing robotized ICSI on an oocyte by an operator is proposed by Lu et al. (seen. IEEE Trans Biomed Eng. 2011 July; 58(7): 2102-8.doi:10.1109/TBME.2011. 2146781.Epub 2011 Apr. 25. LU et al). A complete ICSI automatic system is described in a patent titled "AUTOMATED INTRACYTOPLASMIC SPERM INJECTION ASSISTED FERTILIZATION SYSTEM" (Application No. CN201380021578.9). Due to complexity of the ICSI technology, there are still many problems to be solved in the robotized ICSI and the ICSI automatic system, and thus the ICSI technology can not be applied in clinical applications. The conventional ICSI method is still the only method for the clinical applications due to the relative reliability.

Figure 1:
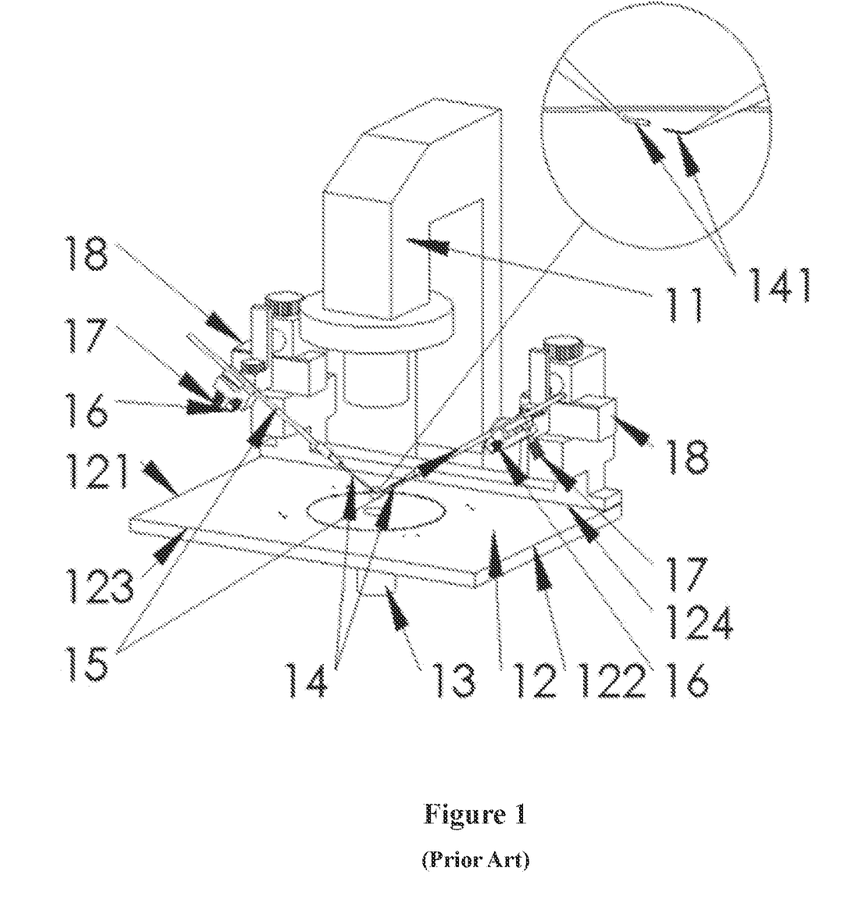
FIG. 1 is a schematic structural diagram showing a relationship between a microneedle and related devices after assembly in a conventional ICSI method.

In the conventional ICSI method, an inverted microscope, a microinjection system and a micromanipulation system form a micromanipulation device. Referring to FIG. 1, the inverted microscope includes basic functional components such as a light source 11, a stage 12, and an objective lens 13. The microinjection system includes basic functional components such as a microneedle 14, a needle holder 15, a needle holder horizontal plane angle adjuster 16, and a needle holder coronal plane angle adjuster 17. The micromanipulation system includes basic functional components such as a needle holder stereo position adjuster 18. The microneedle 14 has a special structure, and includes a slender main body and a functional portion 141. An angle is formed between the functional portion and the main body. FIG. 1 shows a relationship between a microneedle and related devices after assembly in the conventional ICSI method.

For illustration purposes, involved directions are defined as follows. It is assumed that the stage 12 is in a square shape and has four sides including a left edge 121, a right edge 122, a front edge 123, and a back edge 124, as shown in FIG. 1. It is defined that, an X-axis of a reference coordinate system is parallel to the front edge 123 or the back edge 124 of the stage 12, a Y-axis of the reference coordinate system is parallel to the left edge 121 or the right edge 122 of the stage 12, and a Z-axis of the reference coordinate system is perpendicular to the stage 12. The X-axis and the Y-axis form a horizontal plane, the X-axis and the Z-axis form a coronal plane, and the Y-axis and the Z-axis form a sagittal plane. A view parallel to the Y-axis from the near to the distant is defined as a horizontal view, and a view parallel to the Z-axis from the top to the bottom is defined as a plan view.

Figure 2:
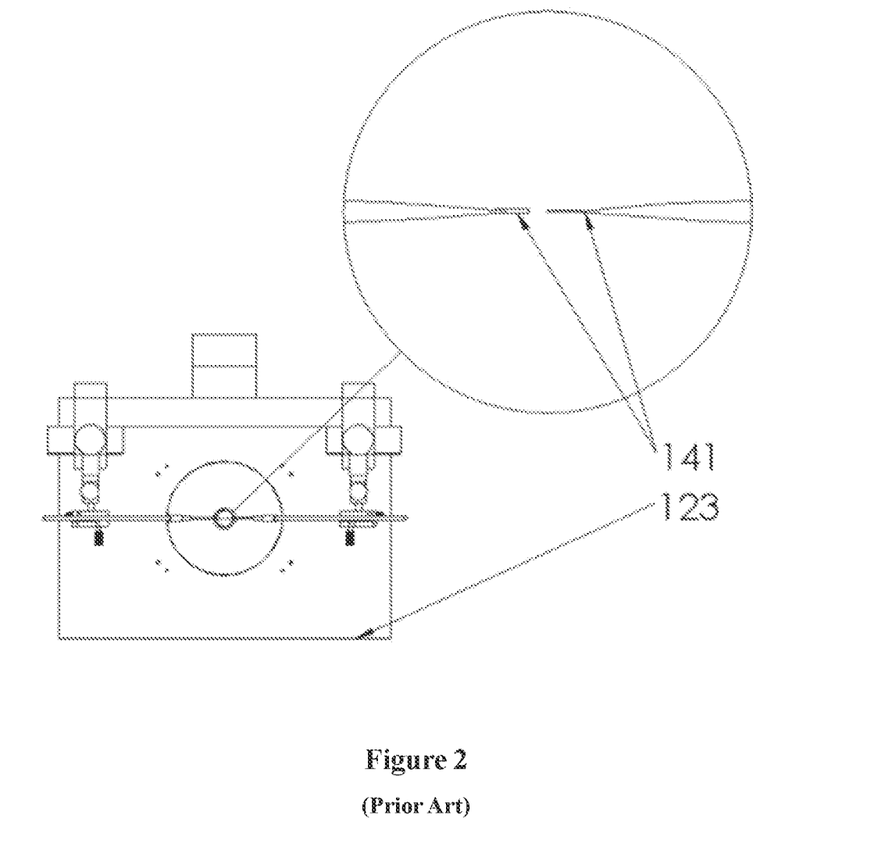
FIG. 2 is a schematic diagram showing a first ideal posture of a microneedle in which a central section of a functional portion of the microneedle is parallel to a coronal plane in a plan view.
Figure 3:
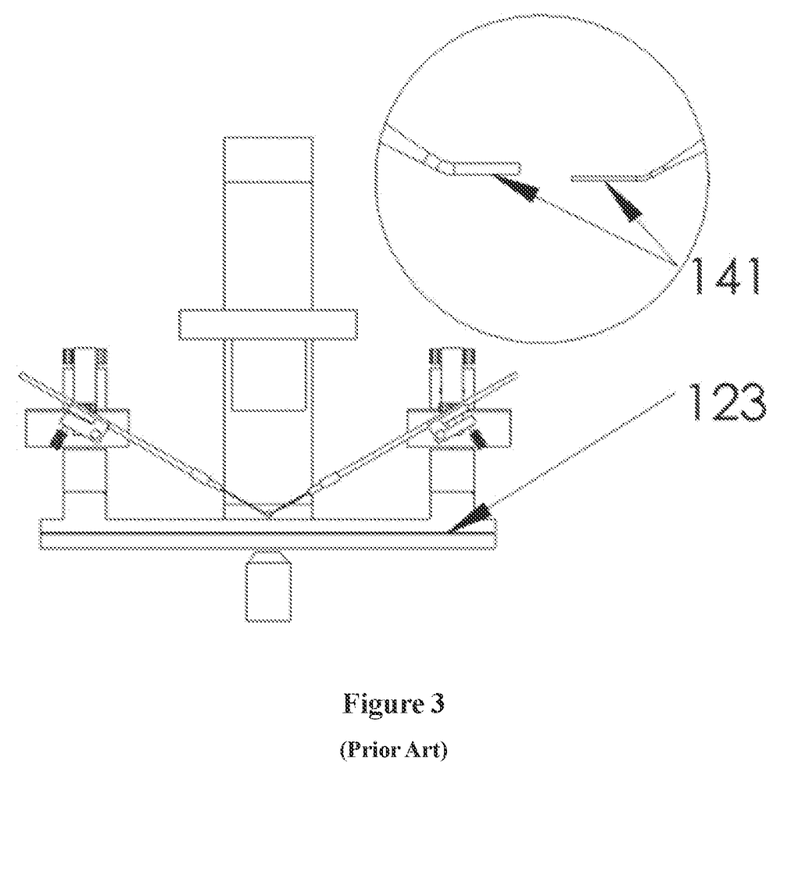
FIG. 3 is a schematic diagram showing a second ideal posture of the microneedle in which a lower edge of the functional portion of the microneedle is parallel to a horizontal plane in a horizontal view.

Mounting requirements for the microneedle 14 are very strict. An ideal posture of the microneedle 14 has a first feature and a second feature. In the first feature, a central section of the functional portion 141 of the microneedle 14 is parallel to the coronal plane in the plan view, as shown in FIG. 2. In the second feature, a lower edge of the functional portion 141 of the microneedle 14 is parallel to the horizontal plane in the horizontal view, as shown in FIG. 3.

The plan view is a conventional view of the microscope, in which whether the central section of the functional portion 141 of the microneedle 14 is parallel to the coronal plane is directly observed. Practically, the microscopic image in the horizontal view shown in FIG. 3 can not be observed due to limitations of the existing optical microscope technology. In this case, whether the posture of the microneedle 14 after assembly is in the ideal posture described in the second feature can not be determined.

The strict requirements for the mounting effect for the microneedle 14 are required by an ideal micromanipulation result. A large angle between the central section of the functional portion 141 of the microneedle 14 and the coronal plane, or a large angle between the lower edge of the functional portion 141 of the microneedle 14 and the horizontal plane results in a large damage to a micromanipulation object, i.e., the oocyte. Further, the micromanipulation process is difficult, resulting in a poor micromanipulation result. In order to achieve the ideal posture of the microneedle, the operator observes via the eyepiece lens in the plan view, and adjusts components such as the needle holder horizontal plane angle adjuster 16, the needle holder coronal plane angle adjuster 17, and the needle holder stereo position adjuster 18. In this way, the first feature, i.e., the posture shown in FIG. 2, can be achieved. However, since the microscopic image of the functional portion 141 of the microneedle 14 cannot be observed in the horizontal view, the angle between the lower edge of the functional portion 141 of the microneedle 14 and the horizontal plane cannot be determined.

Functional portions 141 of different microneedles 14 have different thicknesses. For example, outer diameters of functional portions of a holding pipette, an injection needle, and a biopsy needle that are commonly used are respectively equal to 120 μm, 10 μm, and 40 μm. The functional portions 141 of the different microneedles 14 have different lengths, for example, ranging from 300 μm to 1000 μm. Further, the functional portions 141 of the different microneedles 14 have different angles, which is caused by the fact that a corner between the main body and the functional portion 141 of the microneedle 14 is obtained by artificial calcining. The angles of microneedles of different types or different microneedles of a same type are different. In addition, a distance between the functional portion 141 of the microneedle 14 after assembly and a surface of the stage 12 is short, which is approximately equal to 500 μm. In this case, it is very difficult to determine whether the functional portion 141 of the mounted microneedle 14 is horizontal by naked eyes. It is also difficult to design a super-short-distance camera device to observe the functional portion of the microneedle in the horizontal view.

Currently, the angle between the lower edge of the functional portion 141 of the microneedle 14 and the horizontal plane is determined by the operator completely according to experiences. There are large subjective differences between microneedles 14 of different types assembled by a same operator, and there are still large subjective differences between different microneedles 14 of a same type assembled by a same operator at different times. The importance and the technical status of assembling the microneedle 14 are described in detail at pages 332 to 334 of a monograph named "Practical Manual of In Vitro Fertilization", which are not described herein.

SUMMARY

In view of this, a system and a method for automatically calibrating a posture of a microneedle are provided according to embodiments of the present disclosure, such that the microneedle can be precisely assembled.

In an aspect of the present disclosure, a microscopic mirror imaging device is provided. The microscopic mirror imaging device includes a motion actuator, a mirror image former support and a mirror image former. The motion actuator is fixedly mounted on a microscope stage. One end of the mirror image former support is connected to the motion actuator. The mirror image former includes a plane mirror mounted on the other end of the mirror image former support. An angle formed between a mirror surface of the plane mirror and a horizontal plane of the microscope stage is equal to 45°, and an angle formed between the mirror surface of the plane mirror and a coronal plane of the microscope stage is equal to 45°.

In some embodiments, the plane mirror of the mirror image former is in a rectangular shape.

In some embodiments, the mirror image former support is a rigid physical structure connecting the mirror image former and the motion actuator.

In some embodiments, the motion actuator is configured to control, in an automatic manner using a driver or in a manual manner, the mirror image former support to move from an original position to a predetermined position to form a mirror image.

In some embodiments, the motion actuator is a displacement structure having a linear guide rail and a slider. The linear guide rail is parallel to a sagittal plane of the microscope stage. The mirror image former support is perpendicular to the linear guide rail.

In some embodiments, the motion actuator is a displacement structure having a pivot joint. The pivot joint is connected to an arm of the mirror image former to serve as the mirror image former support. The motion actuator is configured to control, in an automatic manner using a driver or in a manual manner, the mirror image former support to pivot from an original angle to a predetermined angle to form a mirror image.

In some embodiments, the motion actuator includes a return element. The return element is configured to control the mirror image former support to return from the predetermined position to the original position.

In some embodiments, the microscopic mirror imaging device further includes a light source arranged on a side of the plane mirror where the mirror surface of the plane mirror is located. The light source is used to enhance a light intensity in a horizontal view.

In an aspect of the present disclosure, a system for calibrating a posture of a microneedle is provided. The system includes the microscopic mirror imaging device described above, an inverted microscope system, a micromanipulation system, a needle holder rotational driver, a coronal plane angle driver, a sagittal plane angle driver, and a central processing device in which processing software is integrated. The inverted microscope system includes a video image acquirer and a manual or automatic focusing device. The micromanipulation system includes a needle holder, a needle holder anchor, and a driver for driving the needle holder to move forward, backward, left, right, up and down. The needle holder rotational driver is mechanically coupled to the needle holder. The coronal plane angle driver is mechanically coupled to the needle holder anchor. The sagittal plane angle driver is mechanically coupled to the needle holder anchor. The processing software is executed to cause the central processing device to: automatically monitor and control positioning of the mirror image former; control the automatic focusing device to perform automatic focusing; control the video image acquirer to perform image acquiring and analyzing; and control operation of the needle holder rotational driver, the coronal plane angle driver, the sagittal plane angle driver, and the driver for driving the needle holder to move forward, backward, left, right, up and down.

In an aspect of the present disclosure, a calibration method applied to the system for automatically calibrating a posture of a microneedle described above is provided. The calibration method includes:

manually assembling a left microneedle and a right microneedle to needle holders, respectively;

manually fixing the needle holders on needle holder anchors, respectively;

for each microneedle, manually adjusting a functional portion of the microneedle to a central visual field of an eyepiece lens;

starting an automatic calibration mode;

generating a video image of the functional portion of the microneedle in a horizontal plane by using the automatic focusing unit and the driver for driving the needle holder to move forward, backward, left, right, up and down;

acquiring, by the video image acquirer, the video image in the horizontal plane;

analyzing an angle $\alpha$ between a projection on the horizontal plane, of the functional portion of the microneedle in the video image in the horizontal plane and a coronal plane by executing the processing software, and starting the needle holder rotational driver and the sagittal plane angle driver to calibrate the functional portion of the microneedle in the horizontal plane by calibrating the angle $\alpha$ to be equal to zero;

positioning the mirror image former to a predetermined position to form a mirror image;

generating a video image of the functional portion of the microneedle in the coronal plane by using the automatic focusing unit and the driver for driving the needle holder to move forward, backward, left, right, up and down;

acquiring, by the video image acquirer, the video image in the coronal plane;

analyzing an angle $\alpha'$ between a projection on the coronal plane, of the functional portion of the microneedle in the video image in the coronal plane and the horizontal plane by executing the processing software, and starting the coronal plane angle driver to calibrate the functional portion of the microneedle in the coronal plane by calibrating the angle α' to be equal to zero; and returning the mirror image former to an original position, and controlling the micromanipulation system to be in a state ready for an ICSI operation.

In some embodiments, in the automatic calibration mode in the step of starting an automatic calibration mode, a posture of the left microneedle is automatically calibrated before or after a posture of the right microneedle is automatically calibrated; or a posture of the left microneedle is automatically calibrated together with a posture of the right microneedle.

In some embodiments, in the step of positioning the mirror image former to a predetermined position to form a mirror image, a distance between the predetermined position and the functional portion of the microneedle is 0.5 mm.

Compared with the conventional technology, the posture of the functional portion of the microneedle can be calibrated to an ideal posture with the simple structure and the solutions according to embodiments of the present disclosure. In this way, the lower edge of the functional portion of the microneedle can be parallel to the horizontal plane.

BRIEF DESCRIPTION OF THE DRAWINGS

In order to more clearly illustrate embodiments of the present disclosure, the drawings to be used in the description of the embodiments are briefly described below. Apparently, the drawings in the following description show only some embodiments of the present disclosure.

DETAILED DESCRIPTION OF EMBODIMENTS

Embodiments of the present disclosure are described in detail below with reference to the drawings, to make advantages and features of the present disclosure.

A process of calibrating a posture of a microneedle is a process that a posture of a functional portion of the microneedle is calibrated to be in an ideal state in both a plan view and a horizontal view. As described in the background part, a microscopic image of the functional portion of the microneedle in the horizontal view cannot be obtained at present. Therefore, in order to achieve the automatic calibration for the posture of the microneedle, a problem to be solved currently is to how to obtain the microscopic image of the functional portion 141 of the microneedle in the horizontal view in a real time manner.

Figure 4:
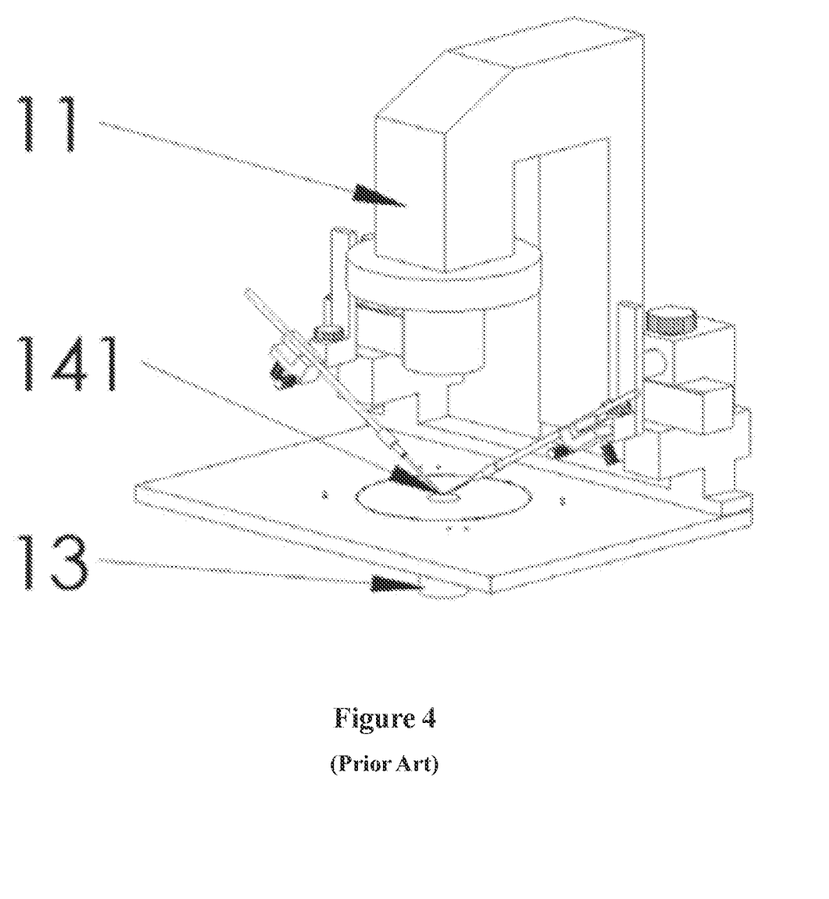
FIG. 4 is a schematic diagram showing a basic imaging principle of a conventional optical microscope.

A basic imaging principle of a conventional optical microscope is described as follows. A light emitted from the light source 11 passes through the functional portion 141 of the transparent microneedle and directly enters an optical imaging system including the objective lens 13, as shown in FIG. 4. In this case, an imaging view is a plan view in the Z-axis direction which is parallel to a transmission direction of the light. The imaging view is single, that is, the formed image is observed only in the plan view.

Based on definitions of the three orthogonal axes (the X-axis, the Y-axis, and the Z-axis) of the reference coordinate system and the three orthogonal reference planes (the horizontal plane, the coronal plane, and the sagittal plane) described in the background part, an intersection line between the horizontal plane and the coronal plane of the microscope stage is the X-axis, an intersection line between the horizontal plane and the sagittal plane of the microscope stage is the Y-axis, and an intersection line between the sagittal plane and the coronal plane of the microscope stage is the Z-axis.

Figure 5:
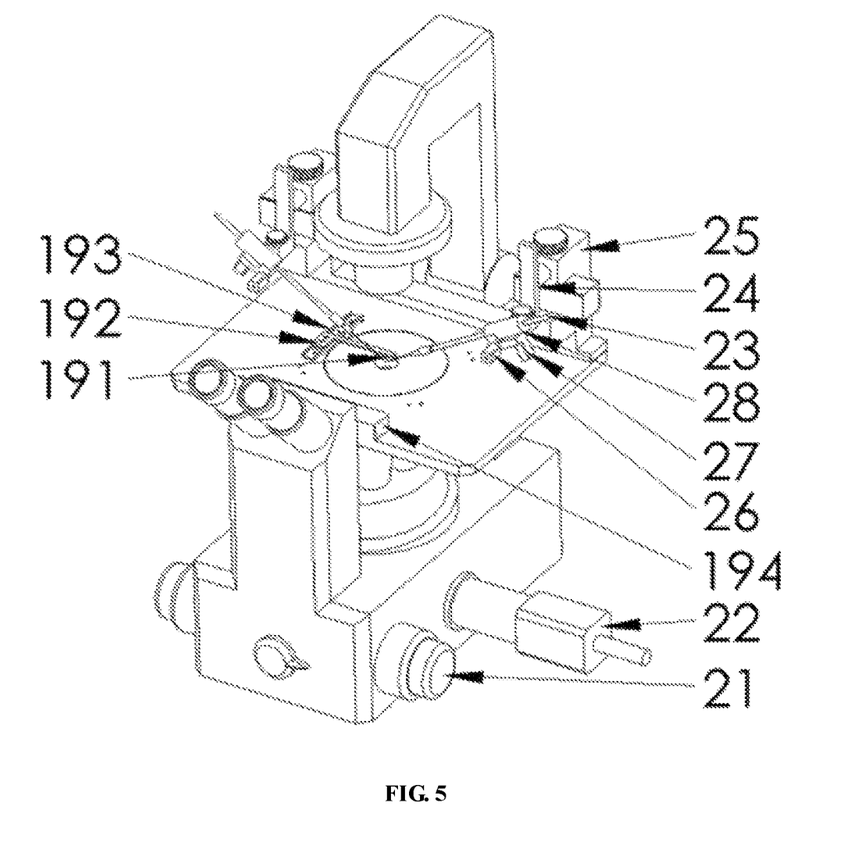
FIG. 5 is a schematic structural diagram showing a system for calibrating a posture of a microneedle according to an embodiment of the present disclosure.
Figure 6:
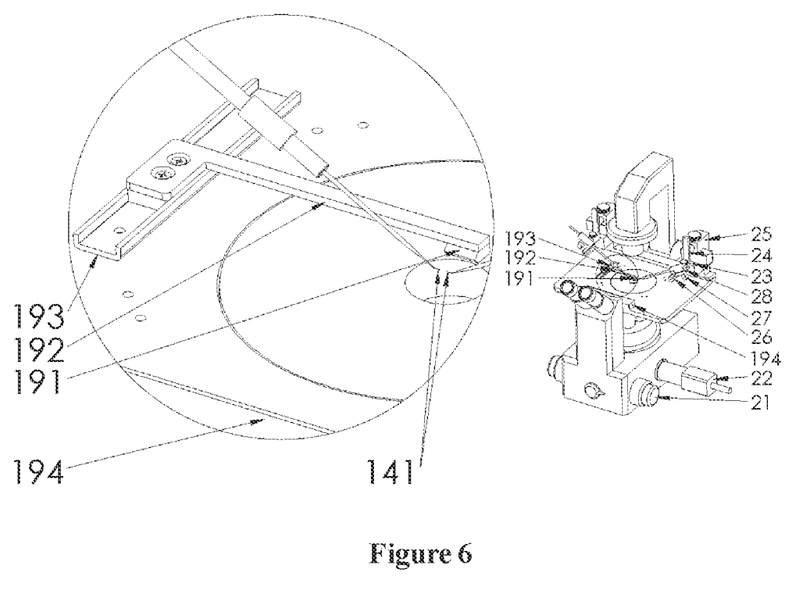
FIG. 6 is a schematic structural diagram showing a microscopic mirror imaging device according to an embodiment of the present disclosure.

In order to obtain the microscopic image of the functional portion 141 of the microneedle in the horizontal view, a microscopic mirror imaging device 19 is provided according to an embodiment of the present disclosure. As shown in FIGS. 5 and 6, the microscopic mirror imaging device 19 includes a mirror image former 191, a mirror image former support 192, and a motion actuator 193. The motion actuator 193 is fixedly mounted on the microscope stage. One end of the mirror image former support 192 is connected to the motion actuator 193. The mirror image former 191 is mounted on the other end of the mirror image former support 192. An angle formed between a mirror surface of a plane mirror of the mirror image former 191 and a horizontal plane of the microscope stage is equal to 45°, and an angle formed between the mirror surface of the plane mirror and the coronal plane of the microscope stage is equal to 45°. In one embodiment, the motion actuator is fixedly mounted on the microscope stage in the Y-axis direction, and the mirror image former support is arranged in the X-axis direction.

The plane mirror serves as a mirror image forming structure of the mirror image former 191 and is used to acquire a mirror image of an observed object in a particular view. The mirror image former 191 may be made of a material such as glass and metal by plane mirror processing. In one embodiment, the plane mirror is in a rectangular shape.

The mirror image former support 192 may be a rigid physical structure connecting the mirror image former 191 and the motion actuator 193.

The motion actuator 193 may be configured to control the mirror image former support 192 to move from an original position to a predetermined position to form a mirror image in an automatic manner using a driver or in a manual manner. For example, the motion actuator 193 is a displacement structure having a linear guide rail and a slider. The linear guide rail is parallel to a sagittal plane of the microscope stage. The mirror image former support is perpendicular to the linear guide rail. In another example, the motion actuator 193 is a displacement structure having a pivot joint. The pivot joint is connected to an arm of the mirror image former to serve as the mirror image former support. The pivot joint is configured to control the mirror image former support to pivot from an original angle to a predetermined angle to form a mirror image in an automatic manner using a driver or in a manual manner.

An object can be accurately moved from an original position to a predetermined position with the motion actuator 193. Further, a return element may be used to control the mirror image former support to return from the predetermined position to the original position.

In one embodiment, the motion actuator may be driven by a driver. In this case, the motion actuator can have an automatic control function.

The microscopic mirror imaging device according to the embodiment of the present disclosure may further include a light source 194 arranged on a side of the plane mirror of the mirror image former 191. The light source 194 is used to enhance a light intensity in the horizontal view. In this way, brightness of the mirror image of the observed object formed on the mirror image former can be effectively increased.

Figure 7:
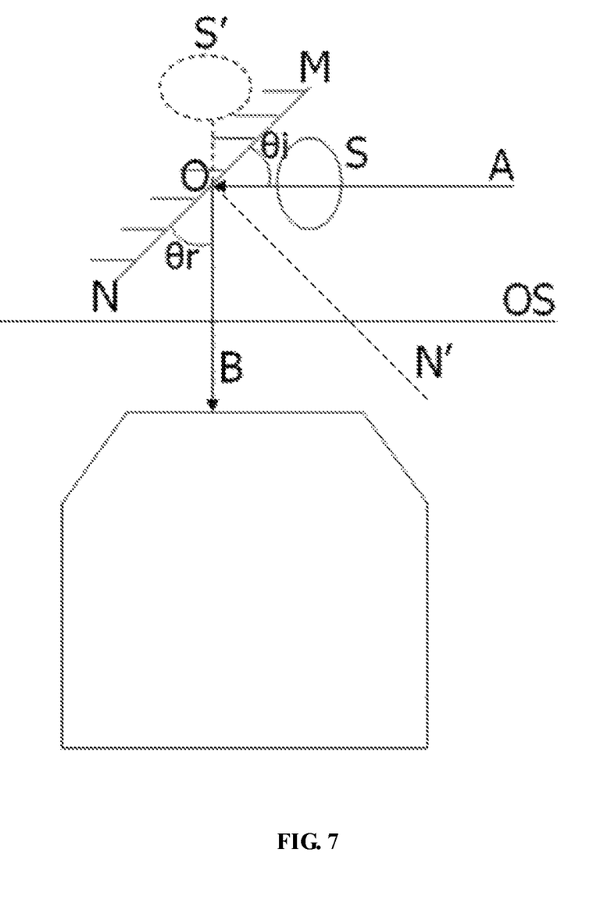
FIG. 7 is a schematic diagram showing a microscopic mirror imaging principle of the microscopic mirror imaging device according to the embodiment of the present disclosure.

A principle of the microscopic mirror imaging device is described as follows. According to plane mirror imaging characteristics, a light is transmitted to the plane mirror after passing through an object (the functional portion 141 of the microneedle in the embodiment of the present disclosure) in a particular view (the horizontal view in the embodiment of the present disclosure), and the light is reflected into an optical imaging system including an objective lens. Thus, a microscopic image of the object is obtained. The image is a microscopic image of a mirror image of the object formed on the plane mirror in the particular view. As shown in FIG. 7, an angle formed between a plane mirror MN and a stage plane (i.e., the horizontal plane) OS is equal to 45°, and an angle formed between the plane mirror MN and the coronal plane is equal to 45°. An incident light A passing through a transparent object S is incident on the plane mirror MN at an incident point O and at an incident angle $\theta_i$, and then is reflected based on a normal line N' at a reflection angle $\theta_r$, to form a reflected light B. The reflected light enters the objective lens. In this case, a microscopic enlarged image of a mirror image S' is obtained.

The mirror image former support 192 and the motion actuator 193 connected with the mirror image former support 192 are used as components for positioning and returning of the mirror image former 191. In this case, a positioning/returning track of the mirror image former 191 is limited by the motion actuator 193 and is parallel to the Y-axis of the microscope stage.

Figure 8:
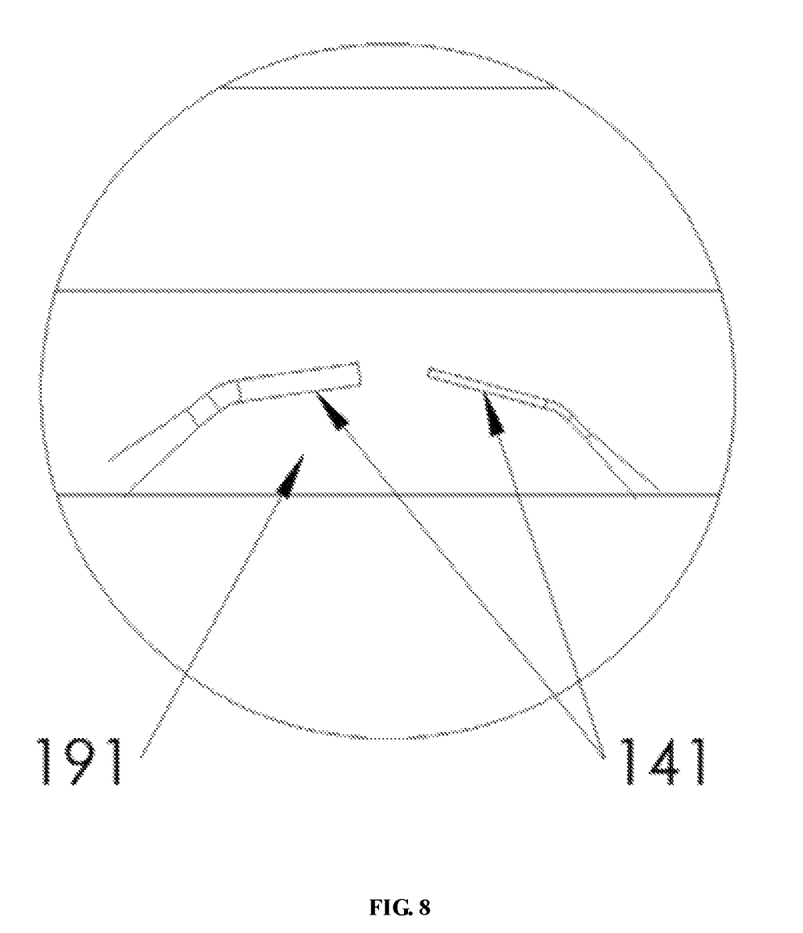
FIG. 8 is a schematic diagram showing a microscopic mirror imaging effect of a functional portion of a microneedle of the microscopic mirror imaging device according to the embodiment of the present disclosure, where a microscopic image of a part of the microneedle mirrored by a mirror image former in a horizontal view is observed via an eyepiece lens.

FIG. 8 shows a microscopic mirror imaging effect. A microscopic image of a part of the microneedle mirrored by the mirror image former in the horizontal view may be observed via an eyepiece lens, and a microscopic image of a part of the microneedle not mirrored by the mirror image former in the horizontal view cannot be observed via the eyepiece lens. Due to the plane mirror imaging characteristics, the image observed via the eyepiece lens is inverted and in mirror-image symmetry with respect to the actual functional portion of the microneedle. It is indicated from a microscopic mirror image in FIG. 8 that a lower edge of the functional portion 141 of the microneedle is not in a horizontal posture.

In the present disclosure, by adding the microscopic mirror imaging device to an existing inverted microscope, the microscopic enlarged image of the functional portion 141 of the microneedle in the horizontal view can be obtained, so that whether the functional portion of the microneedle is in the horizontal posture can be determined, and thus the functional portion of the microneedle can be adjusted correspondingly.

Based on the microscopic mirror imaging device described above, a system for calibrating a posture of a microneedle is further provided according to an embodiment of the present disclosure. The system includes the microscopic mirror imaging device 19 according to the above embodiment, an inverted microscope system, a micromanipulation system, a needle holder rotational driver 28, a coronal plane angle driver 27, a horizontal plane angle driver 26, and a central processing unit in which processing software is integrated. The inverted microscope system includes a video image acquirer 22, and a manual or automatic focusing unit 21. The micromanipulation system includes a needle holder 23, a needle holder anchor 24, and a driver 25 for driving the needle holder to move forward, backward, left, right, up and down. The needle holder rotational driver is mechanically coupled to the needle holder. The coronal plane angle driver is mechanically coupled to the needle holder anchor to replace the needle holder coronal plane angle adjuster 17. The horizontal plane angle driver is mechanically coupled to the needle holder anchor to replace the needle holder horizontal plane angle adjuster 16. The processing software is executed to cause the central processing unit to: automatically monitor and control positioning of the mirror image former; control the automatic focusing unit to perform automatic focusing; control the video image acquirer to perform image acquiring and analyzing; and control operation of the needle holder rotational driver, the coronal plane angle driver, the sagittal plane angle driver, and the driver for driving the needle holder to move forward, backward, left, right, up and down.

Figure 9:
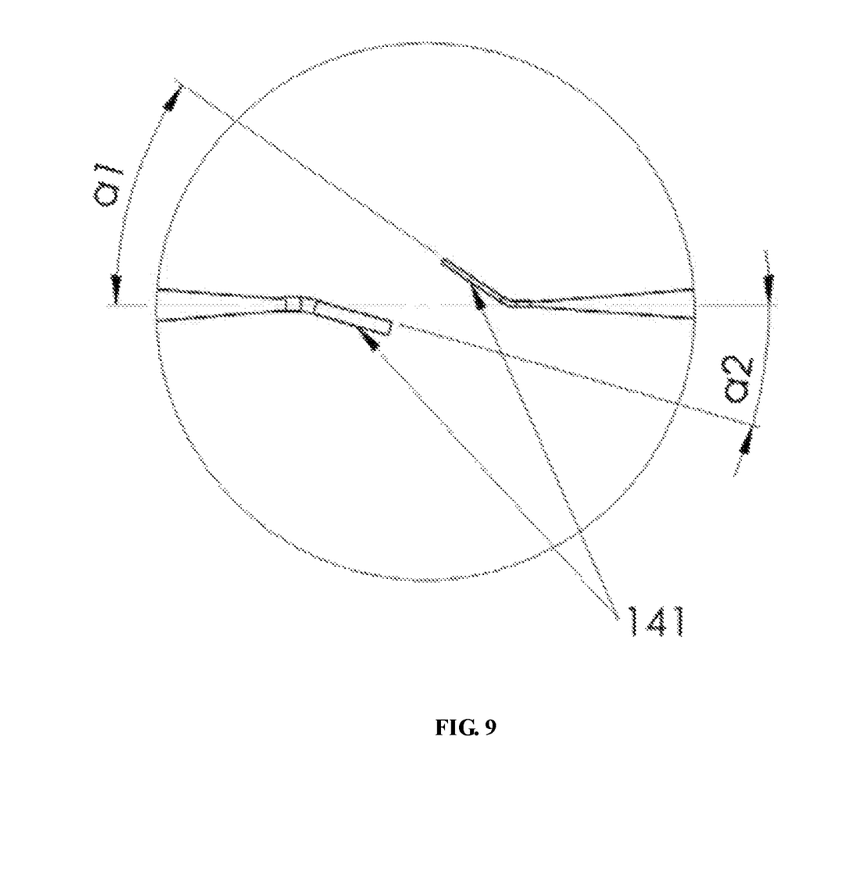
FIG. 9 shows a microscopic image of a functional portion of a microneedle observed in a plan view before the system for calibrating a posture of a microneedle according to the embodiment of the present disclosure performs calibration.

FIG. 9 shows a microscopic image observed in the plan view before calibration. An angle between a projection on the horizontal plane, of the functional portion of the microneedle and the coronal plane is not equal to zero. That is, an angle between the projection on the horizontal plane, of the functional portion of the microneedle and the X-axis is not equal to zero, i.e., $\alpha1 \neq 0$, and $\alpha2 \neq 0$.

Figure 11:
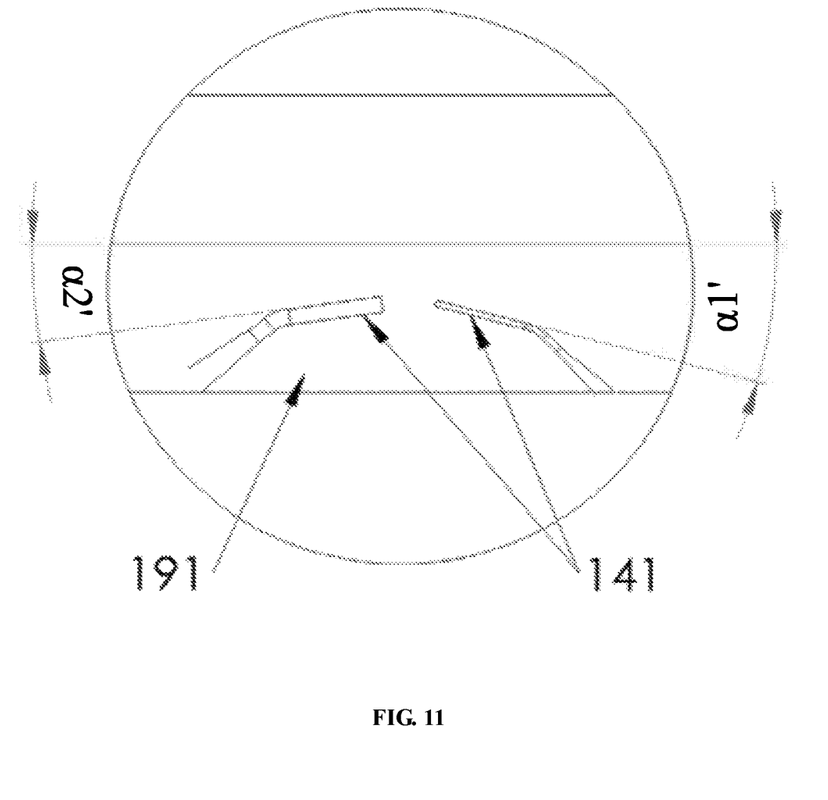
FIG. 11 shows a microscopic mirror image of a functional portion of a microneedle observed via an eyepiece lens in a horizontal view before the system for calibrating a posture of a microneedle according to the embodiment of the present disclosure performs calibration.

FIG. 11 shows a microscopic mirror image observed in the horizontal view before calibration. An angle between a projection on the coronal plane, of the lower edge of the functional portion of the microneedle and the horizontal plane is not equal to zero. That is, an angle between the projection on the coronal plane, of the lower edge of the functional portion of the microneedle and the X-axis is not equal to zero, i.e., $\alpha 1'\neq 0$, and $\alpha 2'\neq 0$.

A calibration method, applied to the system for calibrating a posture of a microneedle includes the following steps S1 to S12.

In S1, a left microneedle and a right microneedle are manually assembled to needle holders, respectively.

In S2, the needle holders are manually fixed on needle holder anchors, respectively.

In S3, for each microneedle, a functional portion of the microneedle is manually adjusted to a central visual field of an eyepiece lens.

In S4, an automatic calibration mode is started.

In S5, a video image of the functional portion of the microneedle in a horizontal plane is generated by using the automatic focusing device and the driver for driving the needle holder to move forward, backward, left, right, up and down.

In S6, the video image in the horizontal plane is acquired by the video image acquirer.

In S7, an angle between a projection on the horizontal plane, of the functional portion of the microneedle in the video image in the horizontal plane and a coronal plane, i.e., an angle $\alpha$ between the projection on the horizontal plane, of the functional portion of the microneedle and the X-axis is analyzed by executing the processing software. Then the needle holder rotational driver and the sagittal plane angle driver are started to calibrate the angle $\alpha$ to be equal to zero, so as to calibrate the functional portion of the microneedle in the coronal plane.

In S8, the mirror image former is positioned to a predetermined position to form a mirror image.

In S9, a video image of the functional portion of the microneedle in the coronal plane is generated by using the automatic focusing device and the driver for driving the needle holder to move forward, backward, left, right, up and down.

In S10, the video image in the coronal plane is acquired by the video image acquirer.

In S11, an angle between a projection on the coronal plane, of the functional portion of the microneedle in the video image in the coronal plane and the horizontal plane, i.e., an angle $\alpha'$ between the projection on the coronal plane, of the functional portion of the microneedle and the X-axis is analyzed by executing the processing software. Then the coronal plane angle driver is started to calibrate the angle $\alpha'$ to be equal to zero, so as to calibrate the functional portion of the microneedle in the horizontal plane.

In S12, the mirror image former is returned to an original position, and the micromanipulation system is controlled to be in a state ready for an ICSI operation.

In the automatic calibration mode in step S4, a posture of the left microneedle is automatically calibrated before or after a posture of the right microneedle is automatically calibrated, or the posture of the left microneedle is automatically calibrated together with the posture of the right microneedle.

In step S8, a distance between the predetermined position and the functional portion of the microneedle may be 0.5 mm.

Figure 10:
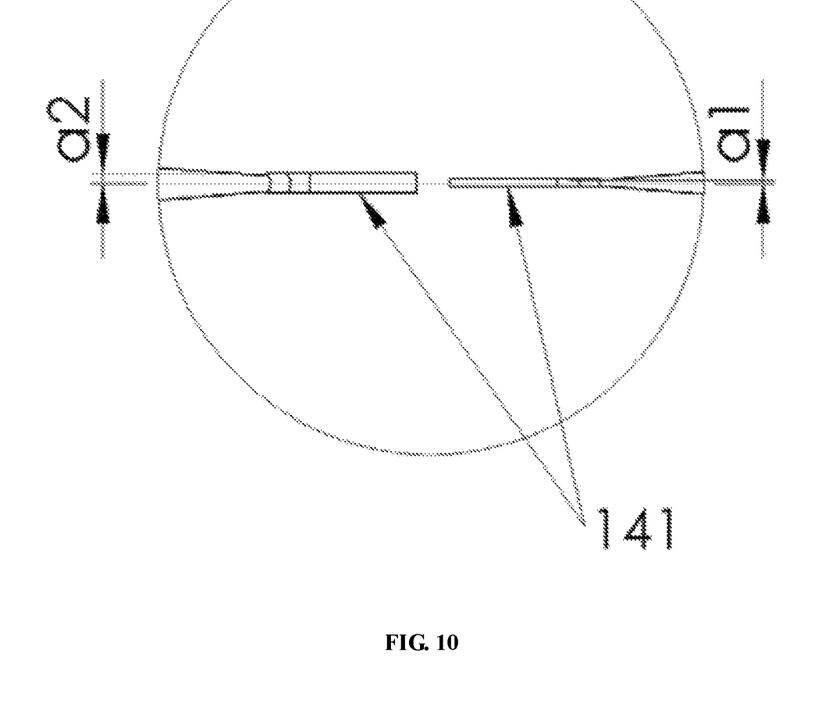
FIG. 10 shows a microscopic image of the functional portion of the microneedle observed in the plan view after the system for calibrating a posture of a microneedle according to the embodiment of the present disclosure performs the calibration.

FIG. 10 shows a microscopic image of the functional portion of the microneedle observed in the plan view after the posture of the microneedle is calibrated by the above adjustment. An angle between a projection on the horizontal plane, of a central section of the functional portion of the microneedle and the coronal plane is equal to zero. That is, an angle between the projection on the horizontal plane, of the central section of the functional portion of the microneedle and the X-axis is equal to zero, i.e., $\alpha 1=0$, and $\alpha 2=0$.

Figure 12:
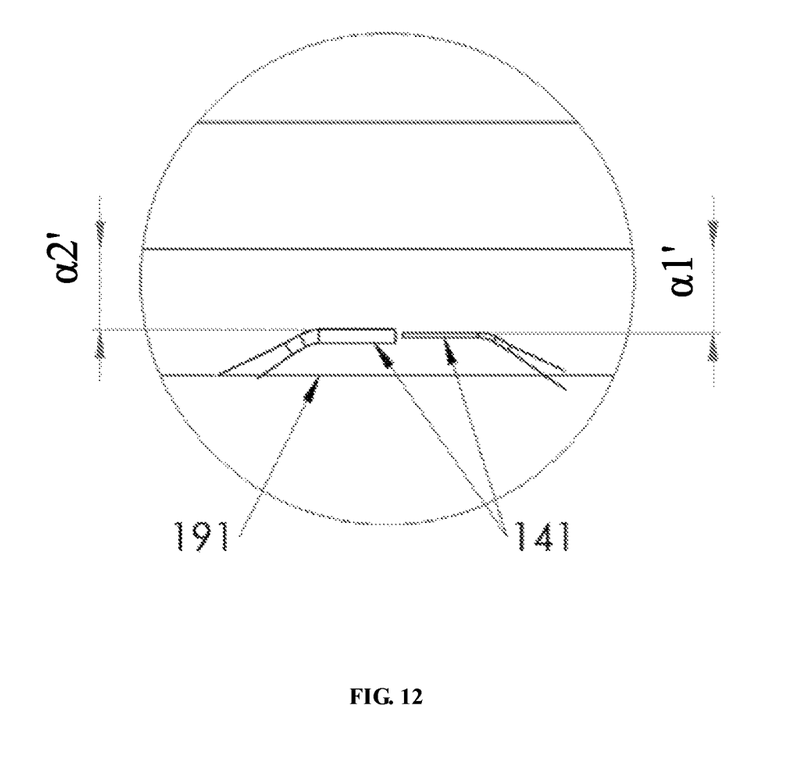
FIG. 12 shows a microscopic mirror image of the functional portion of the microneedle observed via the eyepiece lens in the horizontal view after the system for calibrating a posture of a microneedle according to the embodiment of the present disclosure performs the calibration.

FIG. 12 shows a microscopic mirror image of the functional portion of the microneedle observed via the eyepiece lens in the horizontal view after the posture of the microneedle is calibrated. The angle between the projection on the coronal plane, of the lower edge of the functional portion of the microneedle and the horizontal plane is equal to zero. That is, the angle between the projection on the coronal plane, of the lower edge of the functional portion of the microneedle and the X-axis is equal to zero, i.e., $\alpha 1'=0$, and $\alpha 2'=0$.

The posture of the functional portion of the microneedle can be calibrated to an ideal posture with the simple structure and the solutions provided in the present disclosure. In this way, the lower edge of the functional portion of the microneedle can be parallel to the horizontal plane.

Although the embodiments of the present disclosure are described with reference to the drawings, various modifications and changes can be made without departing from the protection scope of the appended claims. The modifications and changes fall within the scope of the present disclosure.

The invention claimed is:

1. A microscopic mirror imaging device, comprising:
a motion actuator fixedly mounted on a microscope stage;
a mirror image former support, wherein one end of the mirror image former support is connected to the motion actuator, and the mirror image former support is a bracket having a rigid physical structure for connecting a mirror image former and the motion actuator; and
the mirror image former being a plane mirror mounted on the other end of the mirror image former support, wherein an angle formed between a mirror surface of the plane mirror and a horizontal plane of the microscope stage is equal to 45°, and an angle formed between the mirror surface of the plane mirror and a coronal plane of the microscope stage is equal to 45°;
wherein the motion actuator is moved in an automatic manner using a driver or in a manual manner, such that to drive the mirror image former support to move from an original position to a predetermined position to form a mirror image;
wherein a direction of an X-axis is parallel to a front edge or a back edge of the microscope stage, a direction of a Y-axis is parallel to a left edge or a right edge of the microscope stage, and a direction of a Z-axis is perpendicular to the microscope stage, the X-axis and the Y-axis form the horizontal plane of the microscope stage, the X-axis and the Z-axis form the coronal plane of the microscope stage, and the Y-axis and the Z-axis form a sagittal plane of microscope stage; and
wherein: the motion actuator is a displacement structure having a linear guide rail and a slider, the linear guide rail is parallel to the sagittal plane of the microscope stage, and the mirror image former support is perpendicular to the linear guide rail; or
the motion actuator is a displacement structure having a pivot joint, the pivot joint is connected to an arm of the mirror image former to serve as the mirror image former support; and the motion actuator is moved in an automatic manner using the driver or in a manual manner, such that to drive the mirror image former support to pivot from an original angle to a predetermined angle to form a mirror image.

2. The microscopic mirror imaging device according to claim 1, wherein the plane mirror of the mirror image former is in a rectangular shape.

3. The microscopic mirror imaging device according to claim 1, wherein the motion actuator comprises:
   a return element configured to control the mirror image former support to return from the predetermined position to the original position.

4. The microscopic mirror imaging device according to claim 1, further comprises:
   a light source arranged on a side of the plane mirror where the mirror surface of the plane mirror is located, wherein the light source is used to enhance a light intensity in a horizontal view.

5. The microscopic mirror imaging device according to claim 1, wherein the motion actuator is fixedly mounted on the microscope stage in the direction of the Y-axis, and the mirror image former support is arranged in the direction of the X-axis.

* * * * *